United States Patent
Perng et al.

(10) Patent No.: US 12,304,881 B2
(45) Date of Patent: May 20, 2025

(54) TRIENTINE TETRAHYDROCHLORIDE AND A METHOD OF PREPARATION AND A PHARMACEUTICAL COMPOSITION THEREOF

(71) Applicant: Yu-Jet Co., Ltd., Taipei (TW)

(72) Inventors: Cherng-Yih Perng, Hsinchu County (TW); Ming-Ren Liang, Taoyuan (TW); Yu-Chen Lin, Zhubei (TW); Tai-Yun Feng, Taoyuan (TW)

(73) Assignee: YU-JET CO., LTD, Taipei (TW)

( * ) Notice: Subject to any disclaimer, the term of this patent is extended or adjusted under 35 U.S.C. 154(b) by 0 days.

(21) Appl. No.: 18/172,875

(22) Filed: Feb. 22, 2023

(65) Prior Publication Data

US 2023/0339842 A1   Oct. 26, 2023

(30) Foreign Application Priority Data

Feb. 23, 2022   (TW) .................... 111106476

(51) Int. Cl.
  *C07C 211/14*    (2006.01)
  *C07C 209/90*    (2006.01)

(52) U.S. Cl.
  CPC .......... *C07C 211/14* (2013.01); *C07C 209/90* (2013.01); *C07B 2200/13* (2013.01)

(58) Field of Classification Search
  None
  See application file for complete search history.

(56) References Cited

U.S. PATENT DOCUMENTS 11,117,855 B2 *   9/2021   Morley ................. C07C 209/84

FOREIGN PATENT DOCUMENTS

| CN | 102924289 A | 2/2013 |
| TW | 202002956 A | 1/2020 |
| WO | WO2006027705 A2 | 3/2006 |

* cited by examiner

*Primary Examiner* — Jeffrey S Lundgren
*Assistant Examiner* — Anthony Joseph Seitz
(74) *Attorney, Agent, or Firm* — MUNCY, GEISSLER, OLDS & LOWE, P.C.

(57) ABSTRACT

A method of preparation of trientine tetrahydrochloride crystals in which an anti-solvent at a feeding temperature is added into a trientine tetrahydrochloride solution and stirred for crystallization wherein the feeding temperature ranges from 50° C. to 75° C. and the anti-solvent is an alcohol solvent. A novel trientine tetrahydrochloride featuring XRPD peaks detected at 21.9, 24.8, 25.2, 28.0 and 35.6±0.1° 2θ for stable storage of a pharmaceutical composition manufactured with the trientine tetrahydrochloride.

17 Claims, 9 Drawing Sheets

TRIENTINE TETRAHYDROCHLORIDE AND A METHOD OF PREPARATION AND A PHARMACEUTICAL COMPOSITION THEREOF

REFERENCE TO RELATED APPLICATIONS

The present application is based on, and claims priority from, Taiwan application number 111106476, filed Feb. 23, 2022, the disclosure of which is hereby incorporated by reference herein in its entirety.

BACKGROUND OF THE INVENTION

Field of the Invention

The invention pertains to the field of trientine tetrahydrochloride. More particularly, the invention pertains to synthesis of and applications of trientine tetrahydrochloride.

Description of the Prior Art

Trientine (TETA) with a chemical structure as shown in Formula 1 relies on four nitrogen atoms in its structure to latch onto coppers for excretions of excessive coppers from a human body and the Wilson's disease therapy frequently. Currently, trientine is applicable to treatments and researches based on hydrochloride salts mostly, that is, trientine dihydrochloride (TETA·2HCl) and trientine tetrahydrochloride (TETA·4HCl).

(Formula 1)
, 4 HCl

As disclosed in Patent No. CN102924289B, "a synthetic process of hydrochloric acid trientine", the stability of TETA·2HCl is worse than that of TETA·4HCl. As disclosed in Patent No. TW202002956A, "a crystalline form of triethylenetetramine tetrachloride and its pharmaceutical uses", TETA·4HCl prepared by a method in WO 2006/027705 is characteristic of a crystalline form of Form A. Faded debris are found in tablets manufactured with TETA·4HCl Form A after six-month storage at 40° C. and 75% RH. Comparatively, a tablet manufactured with TETA·4HCl Form B is less faded and more stable over time. However, the method as disclosed in TW202002956A is criticized for its process being complicated and inconvenient due to TETA·4HCl Form B prepared under conditions of low-temperature crystallization and seeding.

Accordingly, the drawbacks to stability of TETA·4HCl and the method to prepare TETA·4HCl in the prior art deserve to be corrected.

SUMMARY OF THE INVENTION

In virtue of the above issue, the present invention is aimed at providing a method of preparation of trientine tetrahydrochloride crystals that comprises step 1: an anti-solvent at a feeding temperature is added into a trientine tetrahydrochloride solution and stirred for crystallization wherein the feeding temperature ranges from 50° C. to 75° C. and the anti-solvent is an alcohol solvent.

To this end, the alcohol solvent may be methanol (MeOH) or ethanol and preferably methanol.

To this end, the stirring is made for a duration of at least one hour at specific temperature ranging from 5° C. to 25° C. and being 15±5° C. preferably.

To this end, the step 1 further comprises drying crystals for LOD (loss on drying) of crystals <1%.

To this end, the step 1 further comprises (a) pre-step 1: a reaction fluid is prepared by mixing a trientine dihydrochloride (TETA·2HCl) solution and an acidic solution for acidification; (b) pre-step 2: the reaction fluid in which an alcohol anti-solvent is added and is stirred for crystallization of crude trientine tetrahydrochloride.

To this end, the reaction fluid features a pH value ≤2.0.

To this end, the alcohol anti-solvent in the pre-step 2 is methanol or ethanol and preferably methanol.

To this end, the stirring in the pre-step 2 is made for duration of at least two hours at specific temperature ranging from 15° C. to 35° C. and being 25±5° C. preferably.

To this end, the pre-step 2 further comprises drying the crude trientine tetrahydrochloride such that LOD (loss on drying) of the crude trientine tetrahydrochloride is <10%.

The present invention is also aimed at providing trientine tetrahydrochloride wherein the trientine tetrahydrochloride crystals feature XRPD peaks are detected at 21.9, 24.8, 25.2, 28.0 and 35.6±0.1° 2θ.

The present invention is also aimed at providing a pharmaceutical composition comprising either the trientine tetrahydrochloride crystals prepared by the method of preparation or the trientine tetrahydrochloride.

To this end, the pharmaceutical composition further comprises a vehicle pharmaceutically acceptable.

To this end, the vehicle comprises a dissolving agent, a diluent, a lubricant, a binding agent, a depolymerizing agent, an effervescent mixture, a dye, a sweetening agent, a wetting agent, or a nontoxic and pharmaceutically inactive substance for pharmaceutical concoction.

To this end, the dissolving agent is selected from cyclodextrin or modified cyclodextrin; the diluent is selected from lactose, dextrose, sucrose, cellulose, corn starch or potato starch; the lubricant is selected from silicon dioxide, talc, stearic acid, magnesium stearate, calcium stearate or polyethylene glycol; the binding agent is selected from starch, tragacanth gum, gelatin, syrup, Arabic gum, sorbitol, methylcellulose, carboxymethyl cellulose or polyvinylpyrrolidone; the depolymerizing agent is selected from starch, alginic acid, alginate or sodium starch glycolate; the wetting agent is selected from lecithin, polysorbate or lauryl sulfate.

To this end, the formulation of the pharmaceutical composition may be a solution, an emulsion, a suspension, powders, a tablet, a pill, a troche or a capsule.

The present invention is also aimed at providing either trientine tetrahydrochloride crystals prepared by the method of preparation or the trientine tetrahydrochloride for preparation of the pharmaceutical composition with which the Wilson's disease is prevented or treated.

In summary, the present invention provides TETA·4HCl crystals Form N and a method of preparation thereof. TETA·4HCl in the present disclosure is easily prepared for a high yield rate. Moreover, as shown in test results, TETA·4HCl crystals Form N and a pharmaceutical composition thereof in the present disclosure is characteristic of good stability and anti-moisture absorption without drawbacks to storages of TETA·4HCl and tablets thereof in the prior art.

BRIEF DESCRIPTION OF THE DRAWINGS

The techniques of present invention would be more understandable from the detailed description given herein below and the accompanying figures are provided for better illustration, and thus description and figures are not limitative for present invention, and wherein.

DETAILED DESCRIPTION OF THE INVENTION

The technical and scientific terminologies in the patent specification are commonly understood by persons skilled in the art unless otherwise specified.

A singular noun joined by "a/an", "one" or "the" in the patent specification or claims may refer to more than one object unless otherwise specified.

The word like "or" or "and" refers to "and/or" unless otherwise specified. Moreover, the word like "comprise" or "include" is an open-ended term. The descriptions in a previous section refer to general involvement but are not interpreted as restrictions to the subject of the present invention.

The terminologies of "therapy", "used in therapy" and other similar terminologies mean any method to moderate, improve, relieve or reverse a patient's diagnosable conditions and/or symptoms correlated with those conditions and prevent those conditions or any related symptoms.

The terminology of "pharmaceutically acceptable" means a substance or a composition and other components of a pharmaceutical concoction thereof being compatible with each other but not aggravating a patient's symptoms.

The terminology of "pharmaceutically acceptable vehicle" comprises one or more types of ingredients selected from: a solvent, an emulsifier, a suspension agent, a decomposing agent, a binding agent, an excipient, a stabilizing agent, a chelating agent, a diluent, a gelling agent, a preservative, a lubricating agent, a surfactant and another similar vehicle applicable to the present invention.

The terminology of "pharmaceutically acceptable excipient" includes, without limitation, at least one ingredient selected from a polymer, a resin, a plasticizer, a padding, a lubricating agent, a diluent, an adhesive, a disintegrant, a solvent, a co-solvent, an interfacial agent, a preservative, a sweetening agent, a flavoring agent, a pharmaceutical-grade dye or pigment and a binding agent.

The terminology of "effective dosage" means a certain dosage for expected biological feedback from a creature but not recovery of the creature. As comprehended by a person with common knowledge in the art, the effective dosage of the pharmaceutical composition may change with following factors like an expected biological endpoint, a bio-activator to be delivered, composition of an encapsulating matrix and a target tissue.

The terminology of "pharmaceutical composition" means a solid or liquid composition with its form, concentration and purity applicable to medicine administration for a patient from whom an expected physiological change is induced after administration; the pharmaceutical composition is sterile and/or non-pyrogenic.

The terminology of "feed" means substances are fed into a reactive tank during a manufacturing process.

The terminology of "in-process control (IPC)" means monitoring and adjustment of a manufacturing process during production.

The terminology of "anti-solvent" means a solvent with which the solubility of a solute is reduced.

The terminology of "acidification" means a solid or a liquid in which appropriate acids are added is acidic and reacts due to acidity.

The terminology of "crystallization" means crystals are derived from solutes supersaturated in a solution.

The terminology of "wash" means a product derived from a manufacturing process is washed by a specific solvent.

The terminology of "loss on drying (LOD)" means the weight loss of a product which was dried to a constant weight.

The terminology of "re-crystallization" means substances or crystals are re-dissolved in a solvent and re-crystallized from a solution.

A method of preparing trientine tetrahydrochloride in the present disclosure includes preparation of crude trientine tetrahydrochloride (crude TETA·4HCl) from TETA·2HCl and further preparation of TETA·4HCl from crude TETA·4HCl, as required.

Preparation of Crude Trientine Tetrahydrochloride (TETA·4HCl):

In one embodiment of the present disclosure for preparation of crude TETA·4HCl, for example, TETA·2HCl is mixed and dissolved in purified water in which an acidic solution is further added for acidification; an anti-solvent is added into the above solution and stirred continuously for crystallization; reacted suspensions are filtered for wash, loss of drying and preparation of crude TETA·4HCl.

During preparation, the anti-solvent can be a solvent in which no TETA·4HCl is dissolved basically. For example, the anti-solvent includes, without limitation, ethanol or methanol and preferably methanol; the acidic solution can be a solution common in acidification. For example, the acidic solution is the hydrochloric acid solution and preferably the hydrochloric acid solution with the concentration of more than 35%.

For effective preparation of crude TETA·4HCl, the weight ratio of TETA·2HCl to purified water ranges from 0.5:1 to preferably 1:1; temperature of acidification ranges from 10° C. to 40° C. and preferably 20±10° C.; the pH value of a reaction liquid for acidification is ≤2.0; temperature of the anti-solvent to be added ranges from 10° C. to 40° C. and preferably 20±10° C.; the weight ratio of the anti-solvent to TETA·2HCl ranges from 2:1 to 6:1 and preferably 4:1; temperature of crystallization ranges from 15° C. to 35° C.

and preferably 25±5° C.; the duration of continuously stirring the solution is at least two hours; the loss of drying (LOD) of a product is less than 10% and preferably not more than 5.0%.

Reparation of Trientine Tetrahydrochloride (TETA·4HCl) Crystals:

In one embodiment of the present disclosure for preparation of TETA·4HCl crystals, for example, crude TETA·4HCl is mixed and dissolved in purified water in which an anti-solvent is further added and stirred continuously for re-crystallization; reacted suspensions are filtered for wash, loss of drying and preparation of TETA·4HCl crystals.

During preparation, the anti-solvent can be a solvent in which no TETA·4HCl is dissolved basically. For example, the anti-solvent includes, without limitation, ethanol or methanol and preferably methanol.

For effective preparation of TETA·4HCl crystals, the weight ratio of crude TETA·4HCl to purified water ranges from 1:1 to 1:2 and preferably 1:1.2; temperature of crude TETA·4HCl dissolved in purified water ranges from 15° C. to 35° C. and preferably 25±5° C.; the weight ratio of crude TETA·4HCl to the anti-solvent ranges from 1:2 to 1:6 and preferably 1:4; temperature of feeding the anti-solvent ranges from 50° C. to 75° C. and preferably 60±5° C.; temperature of continuous stirring ranges from 5° C. to 25° C. and preferably 15±5° C.; the duration of continuous stirring is at least one hour; the loss of drying (LOD) of a product is less than 1% and preferably not more than 0.6%.

A pharmaceutical composition in the present disclosure is based on technologies well known to persons skilled in the art and having common knowledge for preparation of a formulation produced with effective ingredients or composites presented in the present disclosure as well as at least a pharmaceutically acceptable vehicle, as required in the pharmaceutical composition. The formulation includes, without limitation, a solution, an emulsion, a suspension, powders, a tablet, a pill, a troche, a capsule and another similar formulation applicable to the present invention.

Furthermore, the route of administration for the pharmaceutical composition in the present disclosure includes, without limitation, oral administration, injection, mucous membrane, transdermal delivery and other similar routes of administration applicable to the pharmaceutical composition in the present disclosure; the route of administration for the pharmaceutical composition is oral administration preferably.

An applicable formulation can be prepared with TETA·4HCl in the present disclosure and at least a vehicle pharmaceutically acceptable by persons skilled in the art and having common knowledge according to existing technologies. For example, a pharmaceutical composition as an oral formulation in one embodiment is prepared in the following steps. Step 1: TETA·4HCl crystals in the present disclosure are ground or granulated as required; step 2: TETA·4HCl crystals and a vehicle pharmaceutically acceptable are combined with each other for development of a mixture as required.

In the case of the oral formulation manufactured as tablets, there are more steps after step 2. Step 3: the mixture is manufactured as tablets after compression; step 4: the tablets are covered with sugar or a thin film as required. In the case of the oral formulation manufactured as capsules or powders, there is one more step to encapsulate the mixture into capsules after step 2. Moreover, there are other basic steps available to manufactures of pharmaceuticals including, without limitation, grinding, granulation, sugar coating or thin film coating.

In the present disclosure, vehicles pharmaceutically acceptable include, without limitation, dissolving agents, diluents, lubricants, binding agents, depolymerizing agents, effervescent mixtures, dyes, sweetening agents, wetting agents, or nontoxic and pharmaceutically inactive substances for pharmaceutical concoction. The dissolving agents include, without limitation, cyclodextrin or modified cyclodextrin; the diluents include, without limitation, lactose, dextrose, sucrose, cellulose, corn starch or potato starch; the lubricants include, without limitation, silicon dioxide, talc, stearic acid, magnesium stearate, calcium stearate or polyethylene glycol; the binding agents include, without limitation, starch, tragacanth gum, gelatin, syrup, Arabic gum, sorbitol, methylcellulose, carboxymethyl cellulose or polyvinylpyrrolidone; the depolymerizing agents include, without limitation, starch, alginic acid, alginate or sodium starch glycolate; the wetting agents include, without limitation, lecithin, polysorbate or lauryl sulfate.

In the present disclosure, the pharmaceutical composition comprises at most 85% (w/w) TETA·4HCl; for example, the pharmaceutical composition comprises 50% (w/w) TETA·4HCl in one embodiment. Moreover, the pharmaceutical composition is sterile and non-pyrogenic preferably.

All materials used in the present disclosure are commercially available unless otherwise specified.

The novelty of the present invention and specific characteristics thereof are disclosed in claims thereafter; the technical features in the present disclosure are comprehended as disclosed in the patent specification and explained in preferred embodiments and drawings based on philosophy of the present invention.

The present invention is explained in the following embodiments which should not be taken as examples to restrict the present invention.

Embodiment 1, Synthesis of TETA·4HCl

Figure 1:
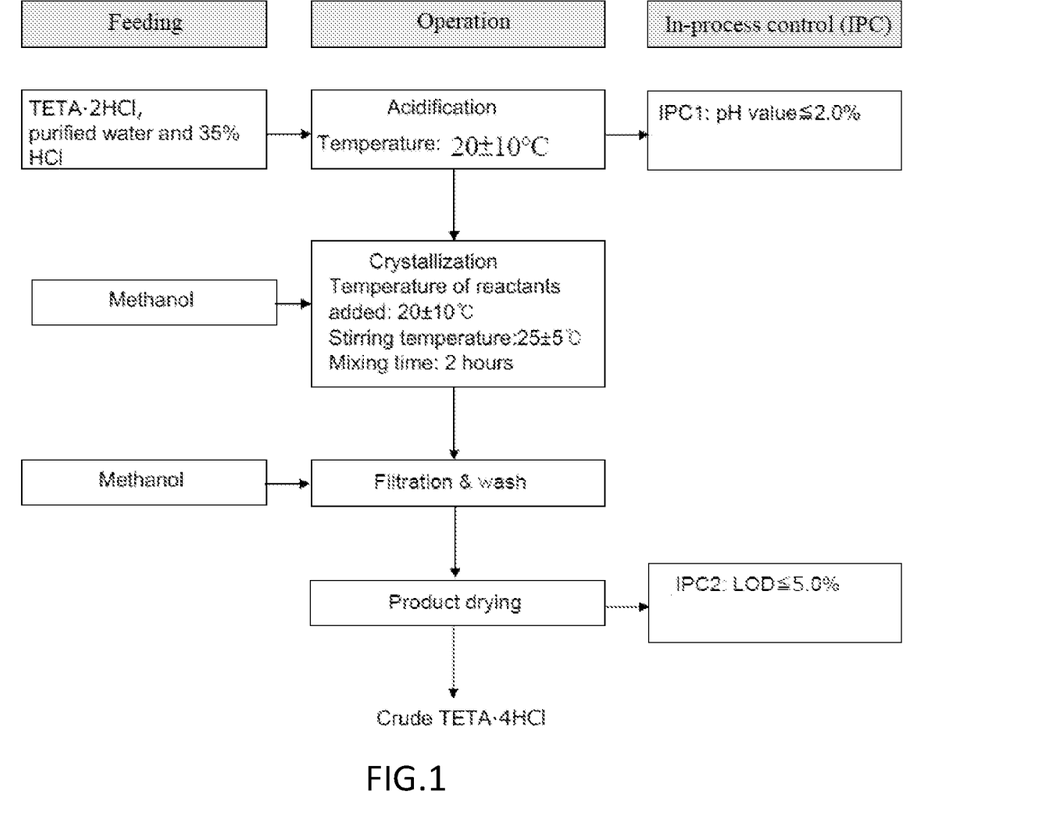
FIG. 1 is a flowchart for preparation of crude TETA·4HCl in the present disclosure.

Preparation of Crude Trientine Tetrahydrochloride (TETA·4HCl):

As shown in the flowchart in FIG. 1, 10 kg trientine dihydrochloride (TETA·2HCl) and 10 kg purified water (PW) are poured into a reactive tank and dissolved at 25±5° C. With temperature of the reactive tank set to 15±5° C., 35% hydrochloric acid (9.45~9.9 kg; 20±10° C.) is added into the reactive tank for acidification at 20±10° C. during which the pH value of the reactive solution is kept at ≤2.0. Then, with temperature of the reactive tank set to 15±5° C., 40 kg methanol (MeOH) with inner temperature of 20±10° C. is added into the reactive tank for crystallization. The reactive tank is further kept at 25±5° C. and reactants in the reactive tank are stirred for at least two hours. Suspensions filtered from the reactive tank are washed twice with 25 kg methanol each time. The final product, crude TETA·4HCl, is derived when LOD is less than 5% after drying.

Figure 2:
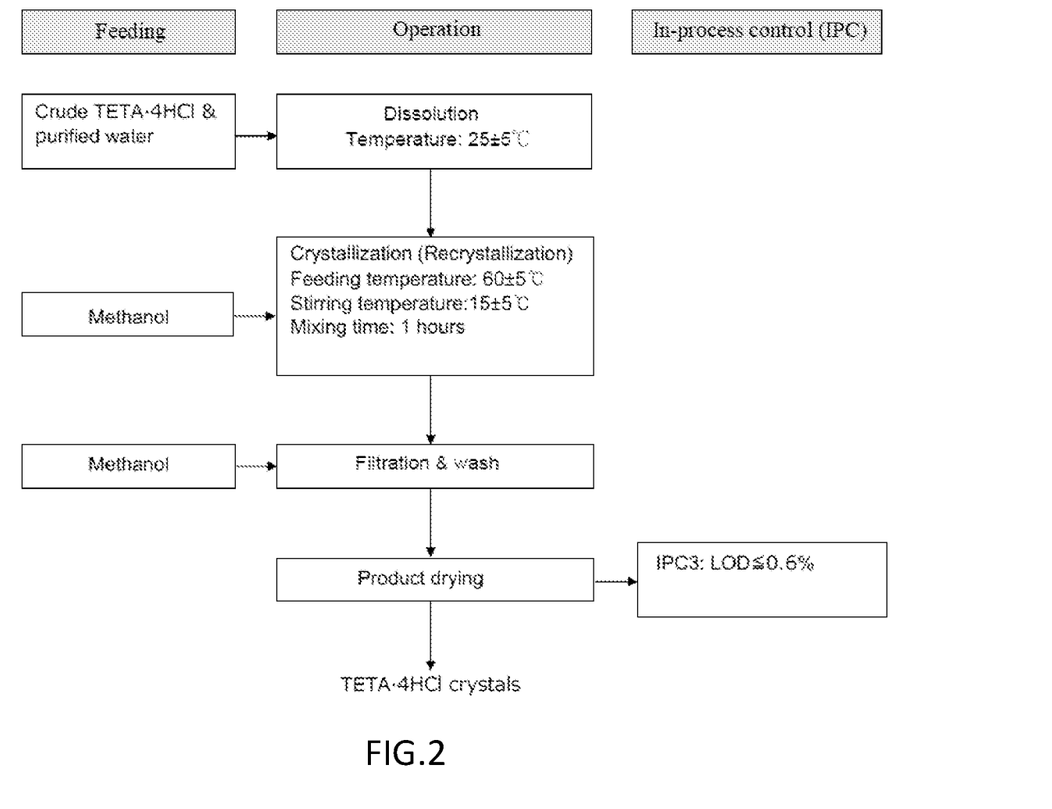
FIG. 2 is a flowchart for preparation of TETA·4HCl crystals in the present disclosure.

Preparation of TETA·4HCl (Trientine Tetrahydrochloride):

As shown in the flowchart in FIG. 2, crude TETA·4HCl derived in the previous process and purified water 1.2 times heavier than crude TETA·4HCl are poured into a reactive tank and dissolved at 25±5° C.; methanol at an amount of four times heavier than crude TETA·4HCl is further added into the reactive tank at 60±5° C. Then, the reactive tank is cooled down and set to 15±5° C. at which reactants in the reactive tank are stirred for at least one hour for re-crystallization. Suspensions in the reactive tank are filtered and washed twice with methanol at an amount of 2.5 times heavier than crude TETA·4HCl each time. The final product, TETA·4HCl, is derived when LOD is less than 0.6% after drying.

Embodiment 2, Analysis of TETA·4HCl Crystals

Figure 3:
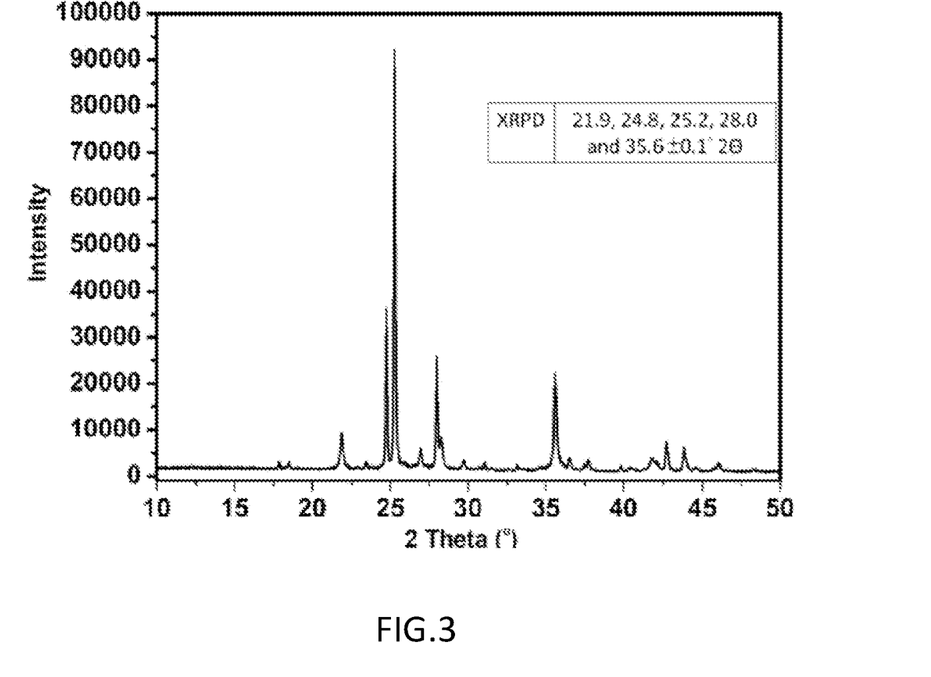
FIG. 3 illustrates test results of the XRPD analysis for TETA·4HCl in one embodiment of the present disclosure.

TETA·4HCl prepared in Embodiment 1 is analyzed with X-Ray Powder Diffraction (XRPD). As shown in FIG. 3 for test results, TETA·4HCl crystals with the XRPD peaks detected at 21.9, 24.8, 25.2, 28.0 and 35.6±0.1° 2θ are designated as Form N.

Embodiment 3, Stability Test 1

According to a method disclosed by the United States Pharmacopeia (USP), impurities inside TETA·4HCl synthesized in Embodiment 1 and kept at distinct temperature (from 25° C. to 40° C.) and relative humidity (from 60% RH to 75% RH) for one month are analyzed with the thin-layer chromatography (TLC) for chromatographic purity. As shown in Table 1 for test results, no impurity inside TETA·4HCl stored at distinct temperature and relative humidity for one month is detected and stability of TETA·4HCl in the present disclosure is good enough.

TABLE 1

|  | Standard | Test result | | |
| --- | --- | --- | --- | --- |
| Chromatographic purity Part I |  | 25° C.; 60% RH | 30° C.; 65% RH | 40° C.; 75% RH |
| Diethylenetriamine (DETA) | Not more than 0.3% w/w | Not detected | Not detected | Not detected |
| 1-(2-Aminoethyl) piperazine (AEP) | Not more than 1.0% w/w | Not detected | Not detected | Not detected |
| Other impurities | Not more than 0.5% w/w | Not detected | Not detected | Not detected |
| Chromatographic purity Part II |  | 25° C.; 60% RH | 30° C.; 65% RH | 40° C.; 65% RH |
| Tris (2-aminoethyl) amine (TAEA) | Not more than 0.5% w/w | Not detected | Not detected | Not detected |

TABLE 1-continued

| Total impurities (Part I & Part II) | Not more than 2.0% w/w | Not detected | Not detected | Not detected |
| --- | --- | --- | --- | --- |

*Not detected: Below Quantification Limit (BQL)

Embodiment 4, Stability Test 2

TETA·4HCl prepared in Embodiment 1 and compressed is manufactured as tablets which are further stored for three months at conditions of 25° C. and 60% RH or 40° C. and 75% RH for analyses of the content of TETA·4HCl and any impurity.

As shown in Table 2 for test results, no significant degradation of TETA·4HCl is detected in the tablets stored for three months and all impurities are identical to those initial impurities and lower than the quantification limit.

TABLE 2

|  |  | Test result | | |
| --- | --- | --- | --- | --- |
| Test item | Standard | Initial quantity | 25° C.; 60% RH | 40° C.; 75% RH |
| Content of TETA·4HCl | 90.0%~110.0% TETA·4HCl (label amount) | 97.5% | 97.4% | 97.5% |
| Piperazine-1,4-diethylamine (Impurity PDEA) | Not more than 0.15% | Not detected | Not detected | Not detected |
| N'-(2-piperazin-1-ylethyl)ethane-1,2-diamine (Impurity PEDA) | Not more than 0.15% | Not detected | Not detected | Not detected |
| Tris (2-aminoethyl) amine (TAEA) | Not more than 0.15% | Not detected | Not detected | Not detected |
| Diethylenetriamine (DETA) | Not more than 0.15% | Not detected | Not detected | Not detected |
| 1-(2-Aminoethyl) piperazine (AEP) | Not more than 0.15% | Not detected | Not detected | Not detected |

*Not detected: Below Quantification Limit (BQL)

Embodiment 5, Moisture Absorption Test

Figure 4:
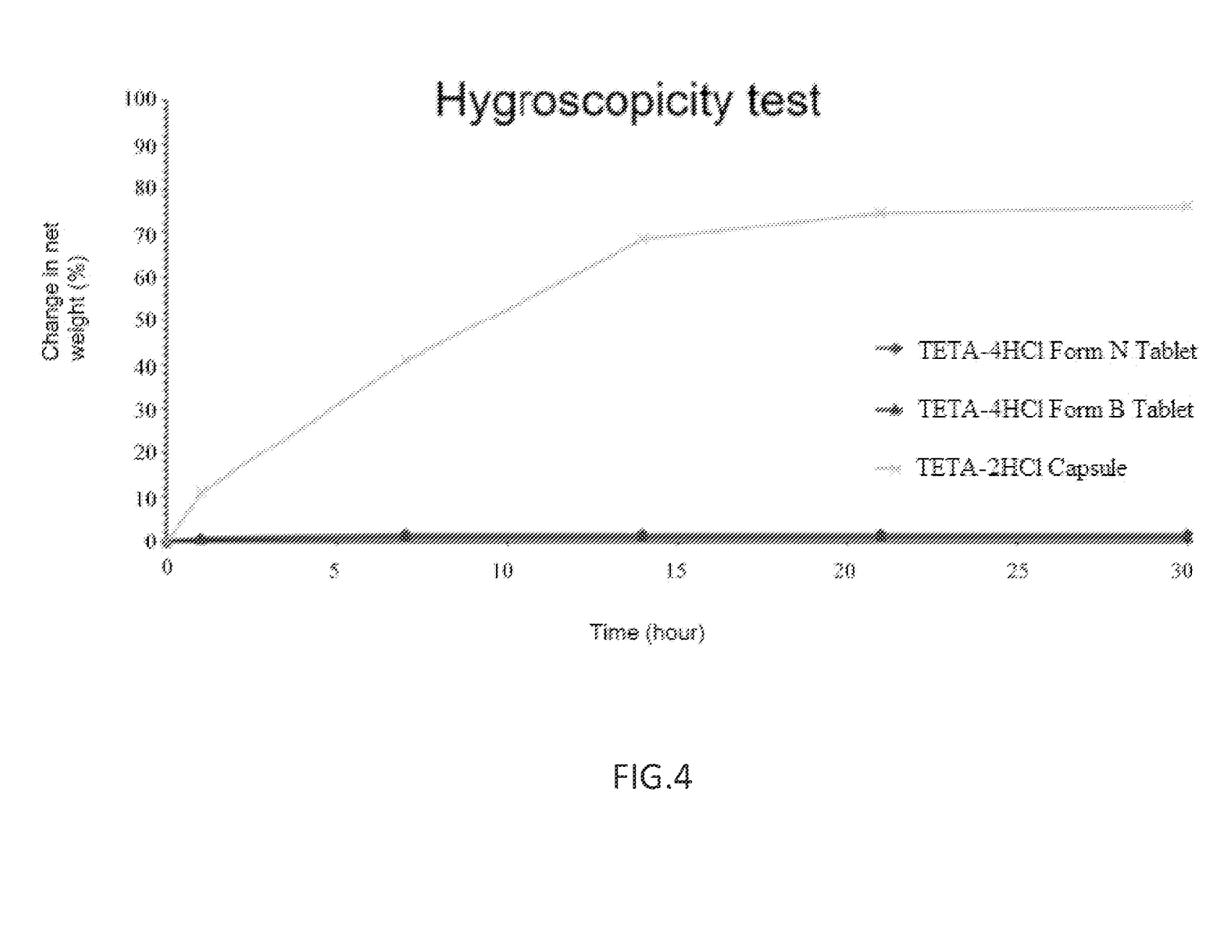
FIG. 4 illustrates test results of moisture absorption of TETA·4HCl tablets in the present disclosure.

The tablets in Embodiment 4 stored for one month at conditions of 25° C. and 75% RH are tested for moisture absorption and compared with other products commercially available, for example, Cuprior® (TETA·4HCl Form B tablets) and TETA·2HCl capsules. As shown in FIG. 4 for test results, no significantly moisture-absorbent and heavier tablet manufactured with TETA·4HCl crystals in the present disclosure is detected but the weight of TETA·2HCl capsules commercially available is 75% heavier than the initial weight due to moisture absorption. It can be seen from test results that tablets manufactured with TETA·4HCl crystals in the present disclosure are effective in anti-moisture absorption.

Embodiment 6, Yield Analysis and Stability Comparison

TETA·4HCl Form N prepared in Embodiment 1 is compared with TETA·4HCl Form B disclosed in Patent TW202002956A.

Figure 5:
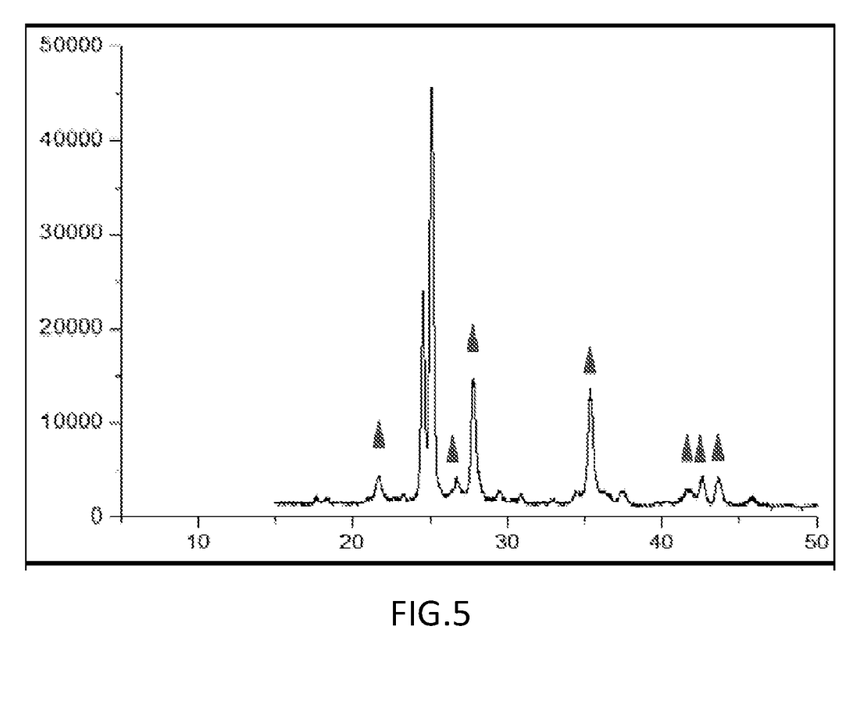
FIG. 5 illustrates test results of the XRPD analysis for TETA·4HCl in one embodiment of the present disclosure.
Figure 6:
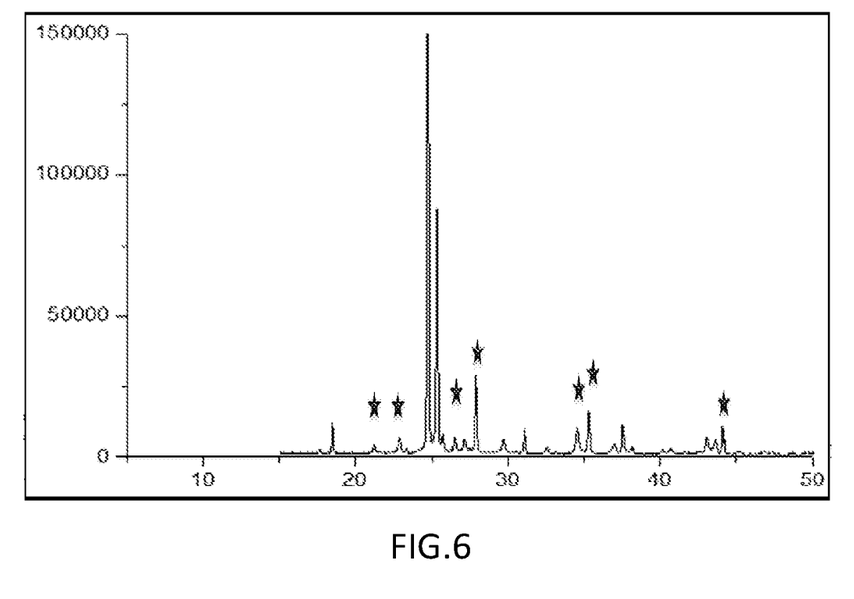
FIG. 6 illustrates test results of the XRPD analysis for TETA·4HCl Form B in Patent No. TW202002956A in one embodiment.
Figure 7:
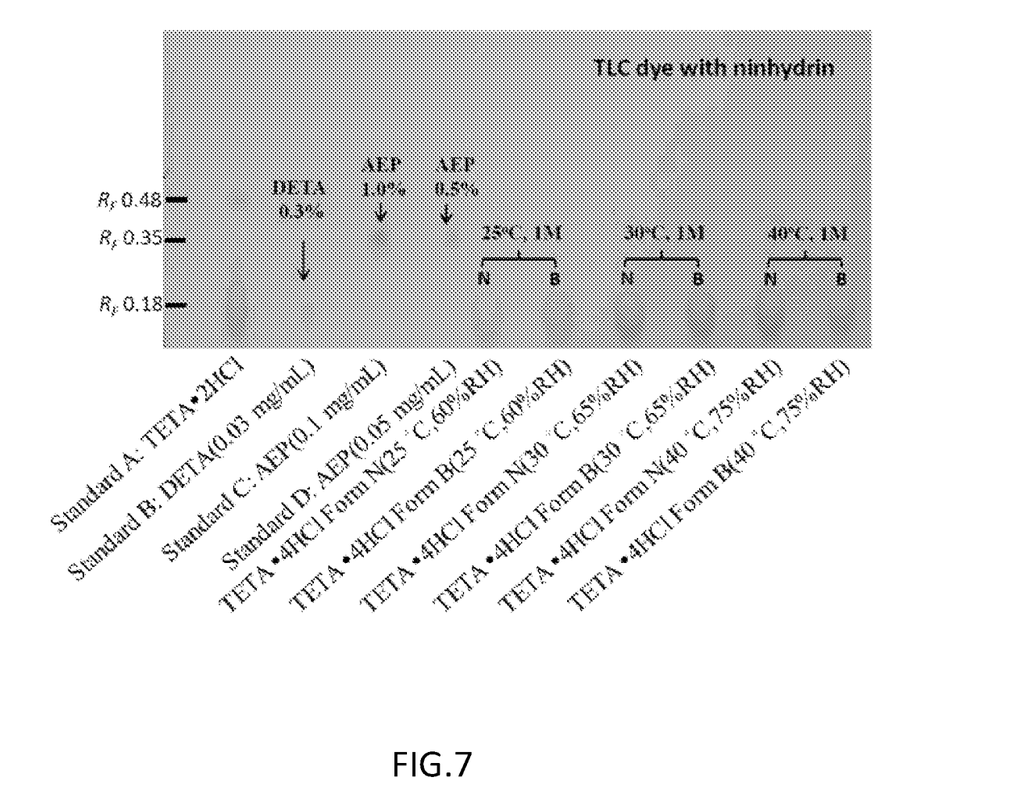
FIG. 7 illustrates test results of stabilities for TETA·4HCl in the present disclosure and TETA·4HCl Form B in Patent No. TW202002956A after one-month storage, respectively.
Figure 8:
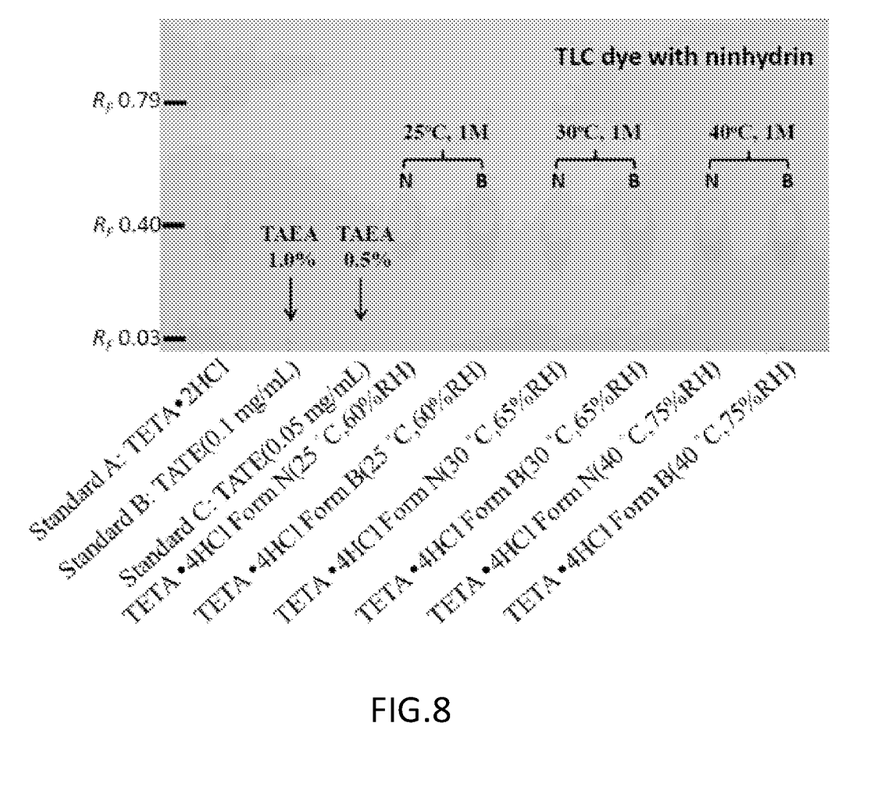
FIG. 8 illustrates test results of stabilities for TETA·4HCl in the present disclosure and TETA·4HCl Form B in Patent No. TW202002956A after one-month storage, respectively.
Figure 9:
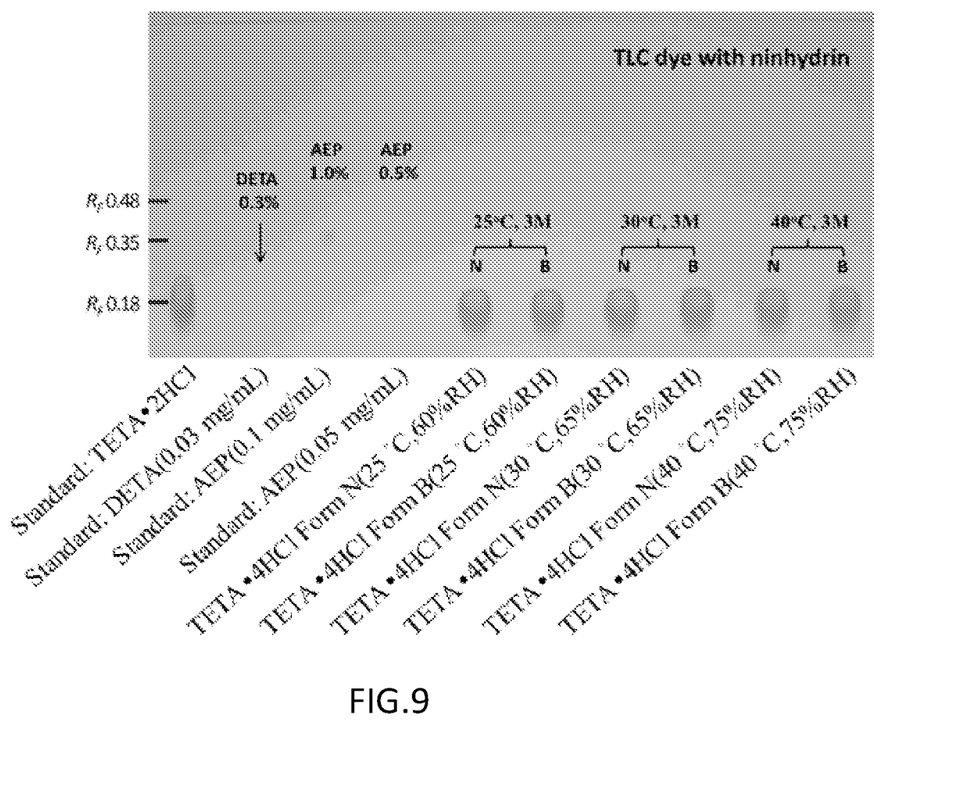
FIG. 9 illustrates test results of stabilities for TETA·4HCl in the present disclosure and TETA·4HCl Form B in Patent No. TW202002956A after three-month storage, respectively.
Figure 10:
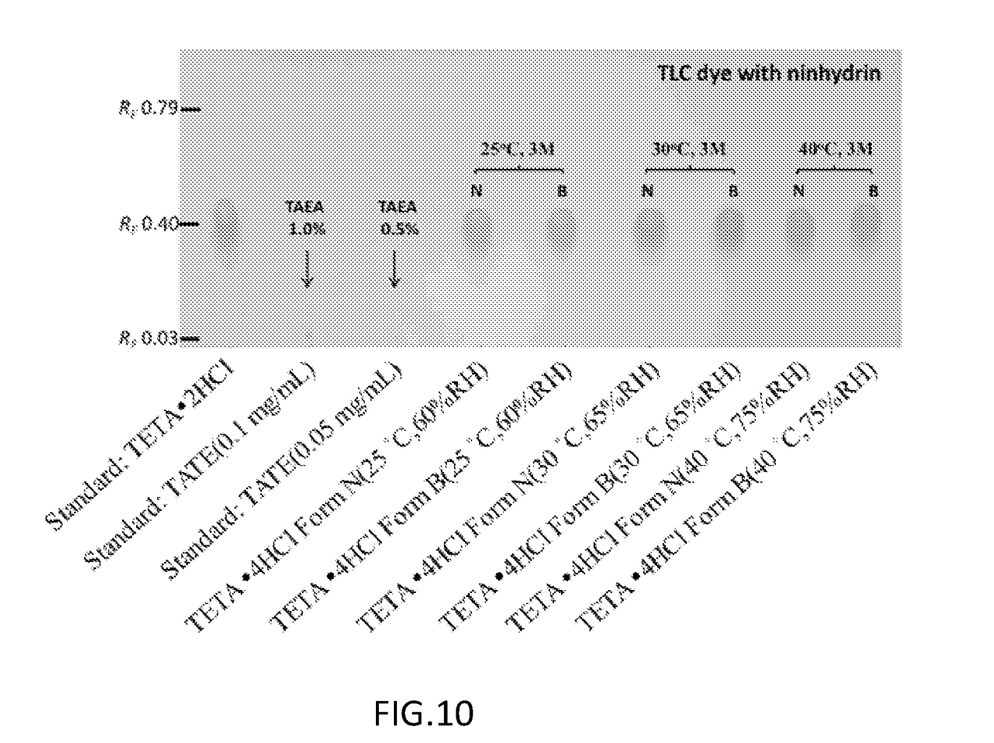
FIG. 10 illustrates test results of stabilities for TETA·4HCl in the present disclosure and TETA·4HCl Form B in Patent No. TW202002956A after three-month storage, respectively.

As shown in FIGS. 5 and 6 for test results of the XRPD analysis, FIG. 5 and FIG. 6 illustrate test results of TETA·4HCl crystals in the present disclosure and TETA·4HCl Form B of Patent TW202002956A, respectively. The yields are shown in Table 3. The yield of TETA·4HCl (Form N) prepared in the present disclosure is unexpectedly high and up to 77.1%~86.6%. Moreover, neither low-temperature crystallization nor seeding is required in the method for preparation of TETA·4HCl crystals in the present disclosure.

TABLE 3

|  | TETA•4HCl in the present disclosure | TETA•4HCl Form B in Patent NO. TW202002956A |
|---|---|---|
| Dissolve solvent | H₂O 1.2 times heavier than crude TETA•4HCl | H₂O 1.2 times heavier than crude TETA•4HCl |
| Anti-solvent | MeOH 4 times heavier than crude TETA•4HCl | EtOH 0.2 times heavier than crude TETA•4HCl |
| Seeding | Nil | 0.5% (w/w) TETA•4HCl Form B |
| Feeding temperature of anti-solvent | 60 ± 5° C. | 10.0° C. |
| Test results of differential scanning calorimetry (DSC) analysis | On-set temperature ($T_{on\text{-}set}$): 270.96° C. Peak temperature ($T_{peak}$): 274.18° C. (Lot No.: SPI-0009-030) | On-set temperature ($T_{on\text{-}set}$): 273.33° C. Peak temperature ($T_{peak}$): 278.14° C. (Lot No.: SPI-0129-193-1) |
| Analytic results of XRPD analysis | Form N | Form B |
| Obtain | 34.6 g~319.0 g | 75.0 g~76.2 g |
| Yield | 77.1%~86.6% | 42.8%~43.1% |

In addition, the purities of TETA·4HCl in the present disclosure and TETA·4HCl Form B, both of which have been stored for one or three months at conditions of temperature from 25° C. to 40° C. and relative humidity from 60% RH to 75% RH, are checked with thin-layer chromatography (TLC) disclosed by the United States Pharmacopeia (USP). As shown in FIG. 7 to FIG. 10 for test results of stabilities, the stability of TETA·4HCl in the present disclosure is similar to that of TETA·4HCl Form B.

In summary, a method of preparation of TETA·4HCl in the present disclosure is advantageous to simplifying a manufacturing process and promoting a yield rate. Moreover, TETA·4HCl Form N prepared by the method of preparation and a pharmaceutical composition thereof in the present disclosure are characteristic of good stability and anti-moisture absorption without a drawback to stability of TETA·4HCl as disclosed in the prior art.

As disclosed in the preferred embodiments of the patent specification, the embodiments are only examples well known to persons skilled in the art and having common knowledge. Any change or modification of the technical features in the patent specification made by persons skilled in the art and having common knowledge should not be taken as differences from the features in the present disclosure. The present invention could be fulfilled based on embodiments in the patent specification and even other changes in embodiments. As defined in claims of the patent specification, the scope of the present invention should cover the method of preparation and any equivalent modification.

As presented in many embodiments hereinbefore, a method of preparation of trientine tetrahydrochloride in the specification meets novelty and non-obviousness for patentability.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of preparation of trientine tetrahydrochloride crystals, comprising:
    step 1: adding an anti-solvent at a feeding temperature into a trientine tetrahydrochloride solution and stirring for crystallization;
    wherein the feeding temperature ranges from 50° C. to 75° C. and the anti-solvent is an alcohol solvent,
    wherein the stirring is made for a duration of at least one hour at a temperature ranging from 5° C. to 25° C.,
    wherein the method does not require a use of seed crystals, and
    wherein the trientine tetrahydrochloride crystals feature X-Ray Powder Diffraction (XRPD) peaks detected at 21.9, 24.8, 25.2, 28.0 and 35.6±0.1° 2θ.

2. The method of preparation as claimed in claim 1, wherein the anti-solvent is methanol.

3. The method of preparation as claimed in claim 2, wherein the step 1 further comprises drying crystals for LOD (loss on drying) of crystals <1%.

4. The method of preparation as claimed in claim 1, wherein the step 1 further comprises:
    pre-step 1: preparing a reaction fluid by mixing a trientine dihydrochloride (TETA·2HCl) solution and an acidic solution for acidification; and
    pre-step 2: adding an alcohol anti-solvent to the reaction fluid and stirring the reaction fluid for crystallization of crude trientine tetrahydrochloride.

5. The method of preparation as claimed in claim 4, wherein the reaction fluid has a pH value ≤2.0.

6. The method of preparation as claimed in claim 4, wherein the alcohol anti-solvent in the pre-step 2 is methanol.

7. The method of preparation as claimed in claim 4, wherein the stirring in the pre-step 2 is made for a duration of at least two hours at a temperature ranging from 15° C. to 35° C.

8. The method of preparation as claimed in claim 4, wherein the pre-step 2 further comprises drying the crude trientine tetrahydrochloride such that LOD (loss on drying) of the crude trientine tetrahydrochloride is <10%.

9. A pharmaceutical composition, comprising the trientine tetrahydrochloride prepared by the method of preparation as claimed in claim 4.

10. The pharmaceutical composition as claimed in claim 9, wherein the pharmaceutical composition further comprises a vehicle pharmaceutically acceptable.

11. The pharmaceutical composition as claimed in claim 10, wherein the vehicle comprises a dissolving agent, a diluent, a lubricant, a binding agent, a depolymerizing agent, an effervescent mixture, a dye, a sweetening agent, a wetting agent, or a nontoxic and pharmaceutically inactive substance for pharmaceutical concoction.

12. The pharmaceutical composition as claimed in claim 9, wherein a formulation of the pharmaceutical composition is a solution, an emulsion, a suspension, powders, a tablet, a pill, a troche or a capsule.

13. The trientine tetrahydrochloride prepared by the method of preparation as claimed in claim 5 for preparation of a pharmaceutical composition with which a Wilson's disease is prevented or treated.

14. A pharmaceutical composition, comprising trientine tetrahydrochloride crystals, wherein the trientine tetrahydrochloride crystals feature X-Ray Powder Diffraction (XRPD) peaks detected at 21.9, 24.8, 25.2, 28.0 and 35.6±0.1° 2θ.

15. The pharmaceutical composition as claimed in claim 14, wherein the pharmaceutical composition further comprises a vehicle pharmaceutically acceptable.

16. The pharmaceutical composition as claimed in claim 15, wherein the vehicle comprises a dissolving agent, a diluent, a lubricant, a binding agent, a depolymerizing agent, an effervescent mixture, a dye, a sweetening agent, a wetting agent, or a nontoxic and pharmaceutically inactive substance for pharmaceutical concoction.

17. The pharmaceutical composition as claimed in claim 14, wherein a formulation of the pharmaceutical composition is a solution, an emulsion, a suspension, powders, a tablet, a pill, a troche or a capsule.

* * * * *